United States Patent
Ohno

(10) Patent No.: US 10,456,017 B2
(45) Date of Patent: Oct. 29, 2019

(54) ENDOSCOPIC CAMERA HEAD AND ENDOSCOPIC DEVICE

(71) Applicant: Sony Olympus Medical Solutions Inc., Tokyo (JP)

(72) Inventor: Naoyuki Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 205 days.

(21) Appl. No.: 15/132,277

(22) Filed: Apr. 19, 2016

(65) Prior Publication Data
US 2016/0323527 A1 Nov. 3, 2016

(30) Foreign Application Priority Data

Apr. 30, 2015 (JP) ................................. 2015-092655

(51) Int. Cl.
*G02B 1/11* (2015.01)
*A61B 1/00* (2006.01)
(Continued)

(52) U.S. Cl.
CPC ...... *A61B 1/00195* (2013.01); *A61B 1/00096* (2013.01); *A61B 1/00163* (2013.01); *A61B 1/042* (2013.01); *G02B 23/2446* (2013.01); *G02B 23/2453* (2013.01); *A61B 1/00105* (2013.01); *G02B 1/11* (2013.01); *G02B 23/2469* (2013.01); *G02B 27/0018* (2013.01); *H04N 2005/2255* (2013.01)

(58) Field of Classification Search
CPC ............ A61B 1/00096; A61B 1/00105; A61B 1/00163; A61B 1/00195; A61B 1/042; G02B 1/11; G02B 23/2453; H04N 2005/2255

USPC ...................................................... 348/45, 47
See application file for complete search history.

(56) References Cited

U.S. PATENT DOCUMENTS 4,905,082 A * 2/1990 Nishigaki .......... A61B 1/00105
348/73
4,998,800 A * 3/1991 Nishida .................. G02B 27/46
348/291
(Continued)

FOREIGN PATENT DOCUMENTS

JP 05-316284 A 11/1993
JP 10-043128 A 2/1998
(Continued)

OTHER PUBLICATIONS

Office Action dated Dec. 18, 2018 in corresponding Japanese Patent Application No. 2015-092655.

*Primary Examiner* — Behrooz M Senfi
(74) *Attorney, Agent, or Firm* — Xsensus LLP

(57) ABSTRACT

There is provided a endoscopic camera head including a cover glass, provided on a connecting face that connects to a base of an endoscope, and disposed to cover an opening for taking into a housing observation light guided inside a lens barrel of the endoscope to the base, and an image sensor configured to receive the observation light passing through the cover glass and entering the housing, and capture an image of a target of observation. In the image sensor, an anti-reflective coating is provided on at least one face of a protective glass disposed facing opposite a light receiving face configured to receive the observation light.

8 Claims, 6 Drawing Sheets

(51) Int. Cl.
  *G02B 23/24* (2006.01)
  *A61B 1/04* (2006.01)
  *G02B 27/00* (2006.01)
  *H04N 5/225* (2006.01)

(56) References Cited

U.S. PATENT DOCUMENTS

| | | | | |
|---|---|---|---|---|
| 6,080,101 A * | 6/2000 | Tatsuno | ............ | A61B 1/00124 |
| | | | | 348/65 |
| 2008/0228035 A1* | 9/2008 | Hagihara | ........... | A61B 1/00071 |
| | | | | 600/121 |
| 2009/0102961 A1* | 4/2009 | Uzawa | ..................... | G02B 9/10 |
| | | | | 348/345 |
| 2010/0268032 A1* | 10/2010 | Seeh | ...................... | A61B 1/002 |
| | | | | 600/169 |
| 2012/0242814 A1* | 9/2012 | Kubala | ..................... | B26F 1/38 |
| | | | | 348/76 |
| 2013/0296649 A1* | 11/2013 | Kirma | ................. | A61B 1/00177 |
| | | | | 600/109 |
| 2015/0238069 A1* | 8/2015 | Osada | ..................... | A61B 1/05 |
| | | | | 600/109 |
| 2017/0202462 A1* | 7/2017 | Motz | ................... | A61B 5/0086 |

FOREIGN PATENT DOCUMENTS

| | | |
|---|---|---|
| JP | 2005-66129 | 3/2005 |
| JP | 2005-099080 A | 4/2005 |
| JP | 2006-053218 A | 2/2006 |

* cited by examiner

ENDOSCOPIC CAMERA HEAD AND ENDOSCOPIC DEVICE

CROSS REFERENCE TO RELATED APPLICATIONS

This application claims the benefit of Japanese Priority Patent Application JP 2015-092655 filed Apr. 30, 2015, the entire contents of which are incorporated herein by reference.

BACKGROUND

The present disclosure relates to an endoscopic camera head.

In the related art, endoscopic devices are known in the medical field as devices for observing the inside of a patient's body cavity. In general, an endoscopic device primarily includes an endoscope having a narrow insertion unit that is inserted into a patient's body cavity, a light source device that supplies the insertion unit with illuminating light that shines onto a target of observation from the tip of the insertion unit of the endoscope, a camera head removably connected to the base of the endoscope, a control device that controls the driving of the camera head, and a display device that displays a captured image.

At the tip of the insertion unit of the endoscope, an illumination window that shines illuminating light onto a target of observation and an observation window that takes in light (observation light) reflected from the target of observation due to the illuminating light are provided. In addition, at the base of the endoscope, an eyepiece with an attached eyepiece lens is provided. Inside the lens barrel of the endoscope, an image guide for observation light is laid out from the observation window at the tip of the insertion unit to the eyepiece at the base of the endoscope. Observation light taken in from the observation window is guided by this image guide to the eyepiece at the base of the endoscope.

The camera head is attached to the eyepiece at the base of the endoscope. Inside the camera head housing, an image sensor and an optical system for condensing observation light onto the image sensor are provided. On the connecting face of the camera head that connects to the eyepiece of the endoscope, an opening for taking observation light into the housing is provided, and a cover glass is disposed on this opening. Observation light enters the camera head housing from the eyepiece of the endoscope through the cover glass, and is condensed onto the image sensor by the optical system provided inside the housing.

By appropriately transmitting a driving signal from the control device to the image sensor of the camera head, the driving of the image sensor is controlled, and an image of the target of observation is captured by the image sensor. The control device performs various types of signal processing on an image signal corresponding to the image of the target of observation captured by the image sensor (captured image) for display of the captured image on the display device. Under control by the control device, the captured image is displayed on the display device on the basis of the image signal that has been subjected to various types of signal processing.

In an endoscopic device having such a configuration, various technologies are being developed to improve the quality of the captured image. For example, JP 2005-66129A discloses technology that uses optical signals to exchange signals such as a driving signal and an image signal between a circuit that comes into contact with the patient (patient circuit), such as the camera head, and all other circuits (secondary circuit), such as the control device, thereby making it possible to electrically insulate the patient circuit and the secondary circuit from each other, while also obtaining a high-quality captured image.

SUMMARY

At this point, when imaging a bright subject with an endoscopic device, for example, a phenomenon called flare may occur, in which the captured image is blown out with white as though light is seeping in, or a phenomenon called ghosting may occur, in which light not originally desired for observation appears in the captured image. To improve the quality of the captured image, further reduction of such flare and ghosting is demanded.

Flare and ghosting are well-known phenomena in typical digital cameras, and the cause is thought to be reflections of observation light in the optical system, such as the lens. Consequently, many attempts have been made to reduce flare and ghosting in endoscopic devices as well by making improvements to the configuration of the optical system, particularly the optical system in the camera head.

However, none of the methods proposed thus far adequately reduces flare and ghosting, and there is still room for improvement. Accordingly, the present disclosure proposes a new and improved endoscopic camera head capable of further improving the quality of the captured image.

According to an embodiment of the present disclosure, there is provided a endoscopic camera head including: a cover glass, provided on a connecting face that connects to a base of an endoscope, and disposed to cover an opening for taking into a housing observation light guided inside a lens barrel of the endoscope to the base; and an image sensor configured to receive the observation light passing through the cover glass and entering the housing, and capture an image of a target of observation. In the image sensor, an anti-reflective coating is provided on at least one face of a protective glass disposed facing opposite a light receiving face configured to receive the observation light.

According to an embodiment of the present disclosure, an anti-reflective coating is provided on the surface of at least one face of a protective glass of an image sensor provided inside an endoscopic camera head. Consequently, the received light intensity on the light receiving face of the photodiode of the image sensor with respect to stray light produced by reflections off the protective glass may be decreased, and flare and ghosting may be reduced. Thus, a higher-quality captured image may be obtained.

According to one or more of embodiments of the present disclosure as described above, it becomes possible to further improve the quality of the captured image. Note that the effects described above are not necessarily limited, and along with or instead of the effects, any effect that is desired to be introduced in the present specification or other effects that can be expected from the present specification may be exhibited.

DETAILED DESCRIPTION OF THE EMBODIMENT(S)

Figure 1:
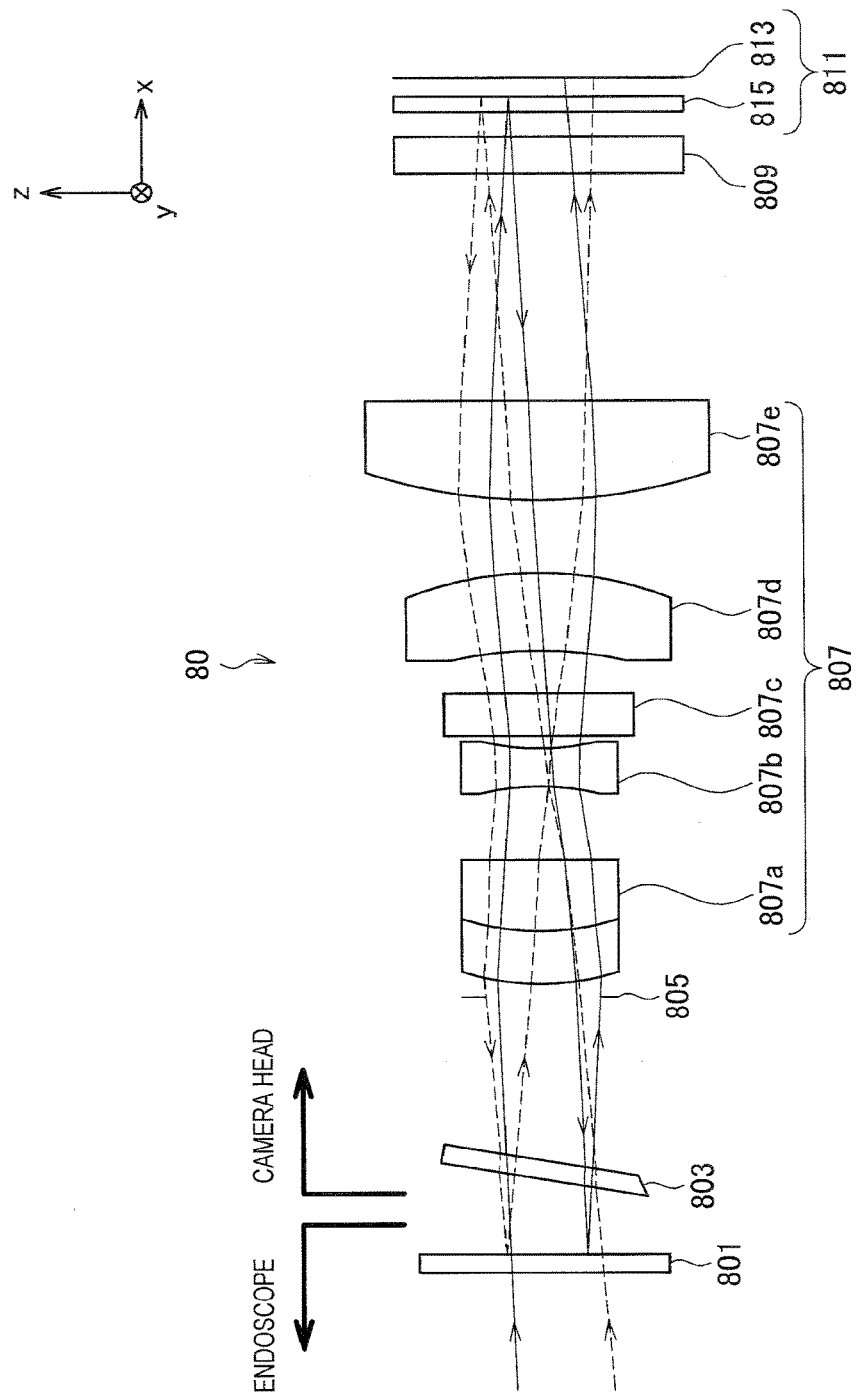
FIG. 1 is a diagram illustrating a result of a ray tracing simulation on an optical system in an existing endoscopic device.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. Investigation of existing configuration
2. First Embodiment
2-1. Configuration of endoscopic device
2-2. Configuration of optical system
3. Second Embodiment
4. Third Embodiment
5. Conclusion
6. Supplemental remarks

1. Investigation of Existing Configuration

Before describing a preferred embodiment of the present disclosure in detail, to further clarify the present disclosure, the results of an investigation by the inventors into the configuration of an endoscope and camera head in an existing endoscopic device will be described, and in addition, the background behind the inventors' conception of the present disclosure will be described.

In an endoscopic device, the insertion unit of an endoscope is inserted into a patient's body cavity, and light (observation light) from a target of observation taken in from the tip of the insertion unit passes through an optical system provided in the endoscope and the camera head, is condensed onto an image sensor provided inside the camera head, and as a result, an image of the target of observation is captured by the image sensor. Note that in the following, the image captured by the image sensor may also be called simply the captured image.

At this point, when imaging a bright subject with an endoscopic device, for example, flare or ghosting may appear in the captured image. Herein, flare refers to a phenomenon in which the captured image is blown out with white as though light is seeping in. Also, ghosting refers to a form of flare, and is an image of light with a more distinct outline. In the following description, for the sake of simplicity, flare and ghosting may also be denoted simply as flare and the like.

Flare and the like may also occur in typical digital cameras, and the cause is known to be reflections of observation light in the optical system, such as the lens. Accordingly, the inventors investigated the occurrence of flare and the like in an existing configuration by performing a ray tracing simulation using a computational model imitating the optical system in an existing endoscopic device.

Note that the occurrence of flare and the like is thought to be influenced by each optical member disposed along the optical pathway from the eyepiece lens provided in the eyepiece at the base of the endoscope to the photodiode of the image sensor inside the camera head. Consequently, to investigate the occurrence of flare and the like, the inventors focused on and analyzed the optical system existing from the eyepiece lens to the photodiode. Namely, the optical system to be analyzed includes the eyepiece lens of the endoscope, the cover glass of the camera head, the optical system provided inside the camera head, such as a lens, and the protective glass of the image sensor. In this way, among the configuration of an endoscopic device, the present disclosure deals with the optical system made up of the various optical members which may contribute to the occurrence of flare and the like existing from the eyepiece lens of the endoscope to the photodiode of the image sensor. In the following description, unless particularly noted otherwise, an optical system simply referred to as the "optical system" is taken to mean the optical system made up of the various optical members existing from the eyepiece lens to the photodiode.

FIG. 1 is a diagram illustrating a result of a ray tracing simulation on an optical system in an existing endoscopic device. In FIG. 1, certain parts of the configuration of the endoscope and the camera head in the existing endoscopic device, such as the lens barrel and housing, are omitted from illustration, and only the optical system that may contribute to the occurrence of flare and the like is extracted for illustration.

Referring to FIG. 1, the optical system 80 in an existing endoscopic device is equipped with an eyepiece lens 801, a cover glass 803, a diaphragm 805, a lens group 807, a filter 809, and a protective glass 815 of an image sensor 811. Note that in FIG. 1, for the sake of clarity, the light receiving face 813 of the photodiode of the image sensor 811 (hereinafter also called simply the light receiving face 813) is also illustrated.

Among this configuration, the eyepiece lens 801 is provided in the endoscope, while the rest of the configuration is provided in the camera head. Observation light taken in from the tip of the endoscope is guided to the base of the endoscope by an image guide laid out inside the lens barrel of the endoscope, passes through the eyepiece lens 801, the cover glass 803, the diaphragm 805, the lens group 807, and the filter 809 in that order, and is incident on the image sensor 811.

Note that in the following description, the direction proceeding from the endoscope to the camera head is also called the x-axis direction. Along the x-axis direction, the direction proceeding from the endoscope to the camera head is denoted as the positive direction. Also, the two directions mutually orthogonal to the plane perpendicular to the x-axis direction are also called the y-axis direction and the z-axis direction, respectively.

The eyepiece lens 801 is provided on the eyepiece at the base of the endoscope.

The cover glass 803 is provided on the connecting face of the housing of the camera head that connects to the eyepiece lens at the base of the endoscope. Observation light enters the housing of the camera head through the cover glass 803. Note that, as discussed earlier, the camera head is configured to be removable from the base of the endoscope, and thus the eyepiece lens 801 of the endoscope and the cover glass 803 of the camera head are sites exposed to the outside.

The diaphragm 805, the lens group 807, the filter 809, and the image sensor 811 are provided inside the housing of the camera head. The diaphragm 805 and the lens group 807 are configured to condense observation light onto the light receiving face 813 of the image sensor 811. In the illustrated example, the lens group 807 is made up of multiple lenses 807a, 807b, 807c, 807d, and 807e.

The filter 809 is a filter for cutting out light of a predetermined wavelength band that may become noise in the captured image.

The image sensor 811 includes components such as a photodiode and a pixel circuit for retrieving an electrical signal that has been opto-electronically converted by the photodiode. By sensing observation light with the photodiode of the image sensor 811, an image of the target of observation is captured by the image sensor 811.

The protective glass 815 is provided on the package of the image sensor 811, at a position facing opposite the light receiving face 813 of the photodiode, and protects the light receiving face 813 from dust, scratches, and the like. Since observation light is incident on the light receiving face 813 through the protective glass 815, the protective glass 815 is also thought to potentially contribute to the occurrence of flare and the like. Consequently, in this analysis, the protective glass 815 is also treated as part of the optical system 80.

In FIG. 1, a representative sample from the results of the ray tracing simulation is illustrated overlaid onto the optical system 80. Referring to the situation illustrated in FIG. 1, incident light entering the camera head from the endoscope and proceeding towards the image sensor 811 (that is, proceeding in the positive x-axis direction) is reflected off the protective glass 815 and proceeds in the opposite direction (that is, in the negative x-axis direction), is reflected again off the eyepiece lens 801, enters the camera head again and proceeds towards the image sensor 811 (that is, in the positive x-axis direction), and finally is incident on the light receiving face 813 of the image sensor 811.

Light exhibiting such behavior is not originally desired to be incident on the light receiving face 813, and from a design standpoint is unintended light (also called stray light). Stray light of a predetermined intensity or more being incident on the light receiving face 813 of the image sensor 811 may cause flare and the like. When imaging a bright subject, the intensity of stray light incident on the light receiving face 813 of the image sensor 811 becomes stronger, and thus flare and the like occurs prominently. Consequently, to moderate the occurrence of flare and the like, it is desirable to decrease the received light intensity of such stray light on the light receiving face 813 of the image sensor 811.

At this point, in a typical digital camera, an image of a target of observation likewise is captured as result of observation light being condensed onto an image sensor by an optical system made up of multiple lenses and other components. Consequently, in a typical digital camera, there is likewise a possibility that stray light may be produced and flare and the like may occur, similarly to the optical system 80 illustrated in FIG. 1.

Accordingly, in general, to moderate the occurrence of flare and the like in a digital camera, an anti-reflective (AR) coating is applied to each optical member constituting the optical system. By providing an anti-reflective coating, reflections off the optical members are moderated, thus making stray light less likely to be produced, and as a result, moderating the occurrence of flare and the like.

Note that generally at this time, from the perspective of cost or other factors, an anti-reflective coating is not provided on the protective glass of the image sensor in many cases. This because even if observation light is reflected off the protective glass of the image sensor, if an AR coat is applied to other optical members and reflections of observation light off the other optical members are moderated, stray light reflected by these other optical members and incident on the image sensor 811 rarely occurs.

However, for an endoscope and a camera head of an endoscopic device, it is difficult to apply the methods used in such typical digital cameras to moderate stray light. The reason for this is because an autoclave process is periodically performed on the endoscope and the camera head for sterilization as medical equipment, and thus even if anti-reflective coatings are provided on the eyepiece lens 801 of the endoscope and the cover glass 803 of the camera head, which are sites exposed to the outside, those anti-reflective coatings will be stripped away by the autoclave process, and the advantageous effects of the anti-reflective coatings will no longer be exhibited.

In this way, in the optical system 80 of an existing endoscopic device, since providing an anti-reflective coating on the eyepiece lens 801 and the cover glass 803 is difficult, stray light reflected by the eyepiece lens 801 and the cover glass 803 and incident on the image sensor 811 occurs.

At this point, in general, to ensure the ability to withstand autoclaving, the eyepiece lens 801 and the cover glass 803 are often formed from sapphire glass. On the other hand, sapphire glass is known to have a greater reflectance compared to typical glass materials. Consequently, in an endoscopic device, there is a tendency for the intensity of stray light produced by reflection off the eyepiece lens 801 and the cover glass 803 to increase compared to a typical digital camera, and there is a risk of flare and the like occurring more prominently.

Accordingly, in a camera head of an endoscopic device according to the related art, to decrease the intensity of stray light reflecting off the eyepiece lens 801 and the cover glass 803 and incident on the image sensor 811, a method of disposing the cover glass 803 tilted by a predetermined angle with respect to a direction orthogonal to the optical axis (namely, the z-axis direction) has been proposed. Such a method has been implemented in the optical system 80 illustrated in FIG. 1.

According to such a method, the cover glass 803 is disposed tilted by a predetermined angle with respect to the protective glass 815 of the image sensor 811, or in other words, disposed so that the cover glass 803 and the protective glass 815 do not become approximately parallel to each other. Consequently, part of the observation light reflected by the protective glass 815 and incident on the cover glass 803 is reflected by the cover glass 803 in a different direction from the incident direction (that is, a different direction from the direction leading to the image sensor 811). In other words, part of the stray light reflected by the cover glass 803 becomes reflected towards the outside of the optical system 80, and thus the intensity of stray light reflected by the cover glass 803 and incident on the image sensor 811 may be decreased.

In this way, by disposing the cover glass 803 at a tilt, in the existing optical system 80, there is a possibility of moderating the production of stray light due to reflections off the cover glass 803. However, even if such a countermeasure is implemented, as illustrated in FIG. 1, in the optical system 80, stray light reflected by the eyepiece lens 801 and incident on the image sensor 811 may still exist as before. In this way, in the existing optical system 80, the occurrence of flare and the like could not be moderated adequately.

The above thus describes the results of an investigation by the inventors into the optical system in an existing endoscopic device. The results of the investigation are summarized as follows.

As described above, in an endoscope and a camera head of an existing endoscopic device, since an autoclave process is conducted, providing an anti-reflective coating on the eyepiece lens 801 and the cover glass 803 exposed to the outside is impractical. Consequently, it is difficult to decrease the intensity of stray light reflected by the eyepiece lens 801 and the cover glass 803 and incident on the image sensor 811, and this difficulty becomes a factor causing flare and the like to be produced more readily compared to a typical digital camera.

Also, to ensure the ability to withstand autoclaving, the eyepiece lens 801 and the cover glass 803 are often formed from sapphire glass, which has a comparatively high reflectance. Consequently, the intensity of stray light reflected by the eyepiece lens 801 and the cover glass 803 and incident on the image sensor 811 becomes even greater, and there is a risk that flare and the like will be produced more prominently. This can be said to be an issue which is specific to endoscopic devices for medical use and which may not occur in other devices such as typical digital cameras.

To address this issue, as a method of decreasing the intensity of stray light incident on the image sensor 811, a method of disposing the cover glass 803 tilted by a predetermined angle with respect to a direction orthogonal to the optical axis (in FIG. 1, the z-axis direction) has been proposed. Although this method may possibly decrease the intensity of stray light reflected by the cover glass 803 and incident on the image sensor 811, stray light reflected by the eyepiece lens 801 of the endoscope connected to the camera head and incident on the image sensor 811 may still exist as before, and thus this method is not considered to adequately moderate the occurrence of flare and the like.

In light of the above circumstances, there is demanded a technology that, by decreasing the intensity of stray light incident on the image sensor 811 in an endoscopic device, further moderates the occurrence of flare and the like, and enables a higher-quality captured image to be obtained. The inventors investigated configurations that may realize such technology, and as a result, conceived of the preferred embodiment of the present disclosure described hereinafter. The following describes a preferred embodiment of the present disclosure conceived by the inventors.

2. First Embodiment

2-1. Configuration of Endoscopic Device

Figure 2:
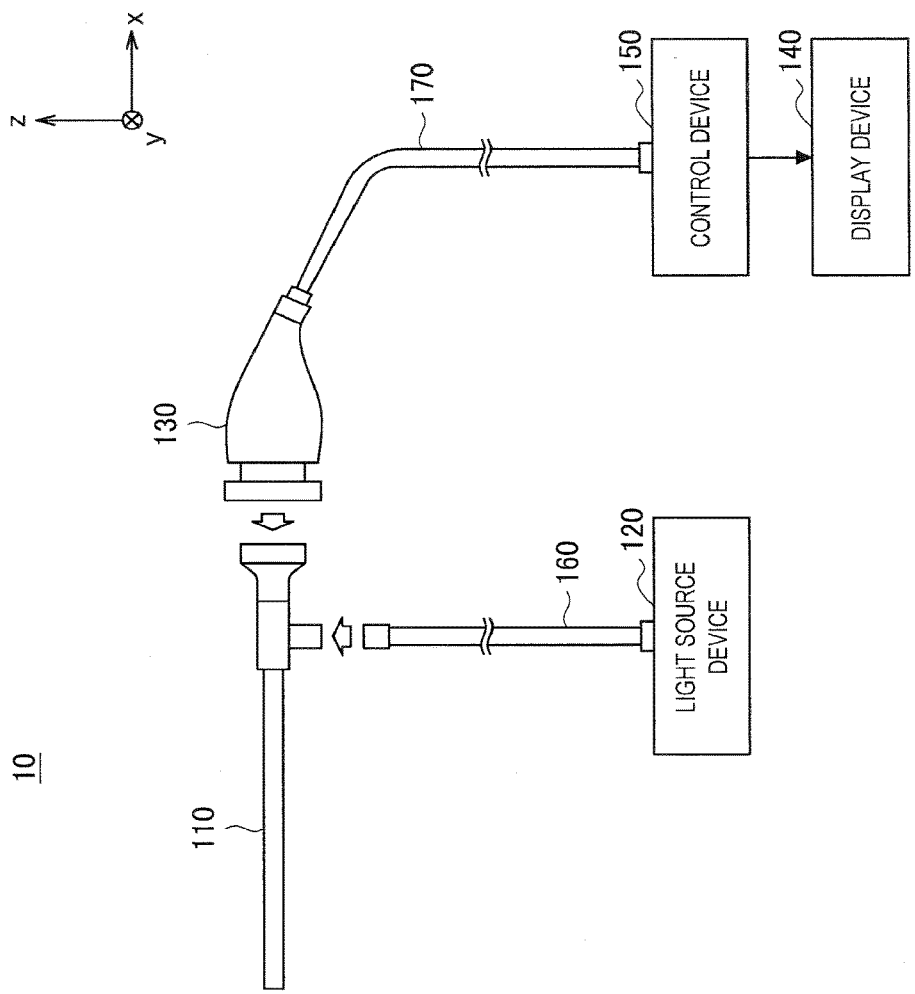
FIG. 2 is a diagram illustrating an example configuration of an endoscopic device according to a first embodiment.

A configuration of an endoscopic device according to the first embodiment of the present disclosure will be described with reference to FIG. 2. FIG. 2 is a diagram illustrating an example configuration of an endoscopic device according to the first embodiment.

Referring to FIG. 2, the endoscopic device 10 according to the first embodiment primarily includes an endoscope 110, a light source device 120, a camera head 130, a display device 140, and a control device 150.

The endoscope 110 is a rigid scope having a narrow insertion unit, and at the tip of the insertion unit, an illumination window that shines illuminating light onto a target of observation and an observation window that captures light (that is, observation light) reflected from the target of observation due to the illuminating light are provided. When capturing an image, the insertion unit of the endoscope 110 is inserted inside a patient's body cavity so that the illumination window and the observation window face the target of observation.

The light source device 120 supplies the insertion unit of the endoscope 110 with illuminating light that shines onto the target of observation during image capture. The insertion unit of the endoscope 110 and the light source device 120 are connected by a light guide 160, and illuminating light is supplied from the light source device 120 to the insertion unit of the endoscope 110 via the light guide 160. Illuminating light supplied from the light source device 120 shines onto the target of observation from the illumination window at the tip of the insertion unit of the endoscope 110. Note that, as illustrated in FIG. 2, one end of the light guide 160 may be removably connected to the endoscope 110.

An objective lens is provided on the observation window at the tip of the insertion unit of the endoscope 110, and observation light is taken into the lens barrel of the endoscope 110 from the observation window through the objective lens. In addition, at the base of the endoscope 110, an eyepiece with an attached eyepiece lens is provided. Inside the lens barrel of the endoscope 110, an image guide for observation light is laid out from the observation window at the tip of the insertion unit to the eyepiece at the base of the endoscope. Observation light taken in from the observation window is guided by this image guide to the eyepiece at the base of the endoscope.

The camera head 130 is removably connected to the base of the endoscope 110. Inside the camera head 130, an image sensor and an optical system for condensing observation light onto the image sensor are provided. On the connecting face of the camera head 130 that connects to the eyepiece of the endoscope 110, an opening for taking observation light into the housing of the camera head 130 is provided, and a cover glass is disposed so as to cover this opening. Observation light enters the housing of the camera head 130 housing from the eyepiece of the endoscope 110 through the cover glass, and is condensed onto the image sensor by the optical system provided inside the housing. By condensing observation light onto the image sensor, an image of the target of observation is captured by the image sensor (in other words, an image signal corresponding to the image of the target of observation is acquired).

The control device 150 controls the driving of the camera head 130 and the display device 140, and causes the display device 140 to display an image of a target of observation captured by the image sensor. Specifically, the control device 150 causes the image sensor to capture an image of a target of observation by transmitting a suitable driving signal to a pixel circuit of the image sensor in the camera head 130. An image signal corresponding to an image of the target of observation acquired by the image sensor is transmitted to the control device 150, and the control device 150 performs various types of signal processing on this image signal. The control device 150 transmits the image signal that has been subjected to various types of signal processing to the display device 140, and causes the display device 140 to display an image of the target of observation.

The camera head 130 and the control device 150 are connected by a cable 170, and driving signals and image signals are exchanged through this cable 170. The cable 170 may be a composite cable including multiple optical fibers and multiple electrical signal cables. For example, image signals may be transmitted as optical signals through the optical fibers, while driving signals may be transmitted as electrical signals through the electrical signal cables.

The above thus describes a configuration of the endoscopic device 10 according to the first embodiment with reference to FIG. 2. Note that the configuration of the endoscopic device 10 is not limited to the example illustrated in FIG. 2. As discussed later, since the characteristic features of the first embodiment are included in the configuration of the optical system of the camera head 130, a configuration similar to existing typical endoscopic devices may also be applied to the portions of the configuration of the endoscopic device 10 other than the configuration of the optical system of the camera head 130.

2-2. Configuration of Optical System

Figure 3:
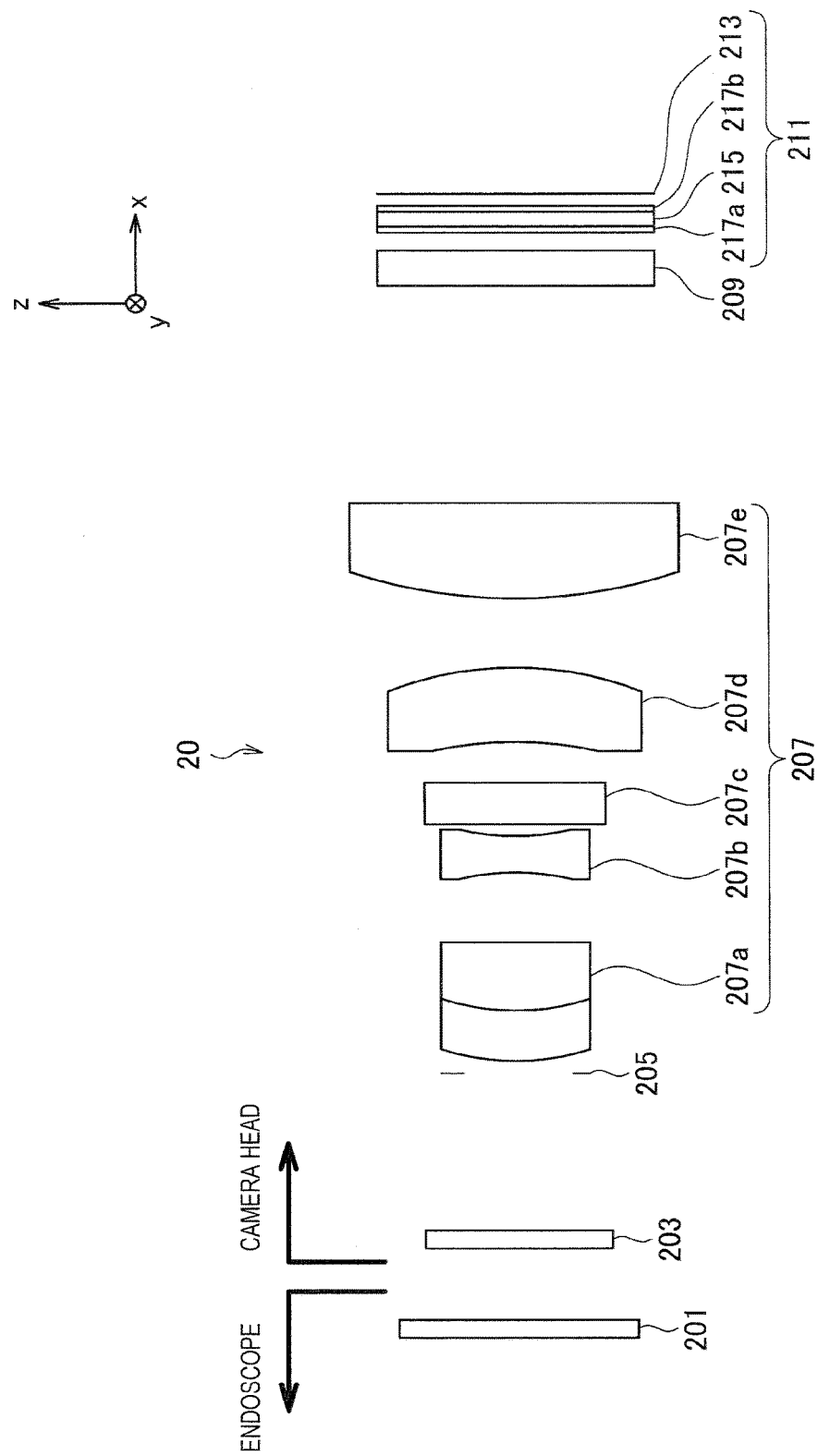
FIG. 3 is a diagram illustrating an example configuration of an optical system according to a first embodiment.

A configuration of the optical system of the endoscopic device 10 according to the first embodiment will be described with reference to FIG. 3. FIG. 3 is a diagram illustrating an example configuration of the optical system according to the first embodiment. Note that FIG. 3 illustrates, as an optical system according to the first embodiment, an optical system made up of the various optical members which may contribute to the occurrence of flare and the like existing from the eyepiece lens of the endoscope 110 to the photodiode of the image sensor in the endoscopic device 10 illustrated in FIG. 2.

Referring to FIG. 3, the optical system 20 according to the first embodiment is equipped with an eyepiece lens 201, a cover glass 203, a diaphragm 205, a lens group 207, a filter 209, and a protective glass 215 of an image sensor 211. Note that in FIG. 3, for the sake of clarity, the light receiving face 213 of the photodiode of the image sensor 211 (hereinafter also called simply the light receiving face 213) is also illustrated.

Among this configuration, the eyepiece lens 201 is provided in the endoscope 110, while the rest of the configuration is provided in the camera head 130. Observation light taken in from the tip of the endoscope is guided to the base of the endoscope by an image guide laid out inside the lens barrel of the endoscope, passes through the eyepiece lens 201, the cover glass 203, the diaphragm 205, the lens group 207, and the filter 209 in that order, and is incident on the image sensor 211.

The eyepiece lens 201 is provided on the eyepiece at the base of the endoscope. Since the camera head 130 is configured to be removable from the base of the endoscope 110, the user is able to detach the camera head 130 from the endoscope 110 as appropriate, and view the target of observation directly through the eyepiece lens 201.

The cover glass 203 is provided on the connecting face of the camera head 130 that connects to the eyepiece at the base of the endoscope 110. The cover glass 203 is disposed to cover the opening in the housing of the camera head 130 for taking observation light into the housing, and observation light enters the housing of the camera head 130 through the cover glass 203. The cover glass 203 fulfills the role of protecting the configuration inside the camera head 130 from the outside environment. For example, because of the cover glass 203, dust and the like is prevented from infiltrating inside the housing of the camera head 130, while in addition, the internal configuration is protected from water vapor and heat during the autoclave process.

Note that, as discussed earlier, the camera head 130 is configured to be removable from the base of the endoscope 110, and thus the eyepiece lens 201 of the endoscope 110 and the cover glass 203 of the camera head 130 are sites exposed to the outside. Consequently, to ensure the ability to withstand autoclaving, the eyepiece lens 201 and the cover glass 203 are preferably formed from sapphire glass.

The diaphragm 205, the lens group 207, the filter 209, and the image sensor 211 are provided inside the housing of the camera head 130. The diaphragm 205 and the lens group 207 are configured to condense observation light onto the light receiving face 213 of the image sensor 211. As an example, FIG. 3 illustrates a lens group 207 made up of five lenses 207a, 207b, 207c, 207d, and 207e. Note that the configuration of the diaphragm 205 and the lens group 207 is not limited to the illustrated example, and features such as the size of the diaphragm 205 and the number and type of lenses constituting the lens group 207 may be designed appropriately so that observation light is efficiently condensed onto the light receiving face 213 of the image sensor 211.

The filter 209 is provided in front of the image sensor 211, and is a filter for cutting out light of a predetermined wavelength band that may become noise in the captured image, such as infrared light, for example. The type of the filter 209 is not particularly limited, and a filter 209 with suitable properties may be selected and used appropriately according to features such as the spectral characteristics of the photodiode of the image sensor 211, so that the desired captured image is obtained.

The image sensor 211 includes components such as a photodiode and a pixel circuit for retrieving an electrical signal that has been opto-electronically converted by the photodiode. The image sensor 211 may be any of various types of known image sensors, such as a charge-coupled device (CCD) image sensor or a complementary metal-oxide-semiconductor (CMOS) image sensor, for example. By sensing observation light with the photodiode of the image sensor 211, an image of the target of observation is captured by the image sensor 211.

The protective glass 215 is provided on the package of the image sensor 211, at a position facing opposite the light receiving face 213 of the photodiode. Specifically, an opening for allowing light to be incident is provided on the package of the image sensor 211 at a site facing opposite the light receiving face 213 of the photodiode, and the protective glass 215 is disposed to cover this opening. The protective glass 215 fulfills the role of preventing dust from sticking to or damaging the light receiving face 213.

For the protective glass 215, low-alpha radiation glass is preferably used to reduce damage to the photodiode. Examples of low-alpha radiation glass materials that may be used for the protective glass 215 include D 263 LA manufactured by Schott (D 263 is a registered trademark), and FP Cover Glass manufactured by Asahi Glass, for example. However, the material of the protective glass 215 is not limited to such examples, and various materials used as the protective glass of typical image sensors may also be applied as the material of the protective glass 215.

Furthermore, in the first embodiment, anti-reflective (AR) coatings 217a and 217b are respectively provided on the surfaces of the protective glass 215. Because of the anti-reflective coatings 217a and 217b, reflections of observation light off the surfaces of the protective glass 215 are moderated, thereby moderating the occurrence of stray light caused by reflections off the surfaces of the protective glass 215, and as a result, also moderating the occurrence of flare and the like.

Note that in the following, for the sake of convenience, the surface of the protective glass 215 that faces the light receiving face 213 may also be referred to as the image-side surface, while the opposite surface (that is, the surface on the side where the target of observation is positioned) may also be referred to as the object-side surface. In the example illustrated in FIG. 3, the anti-reflective coating 217a is provided on the object-side surface of the protective glass 215, while the anti-reflective coating 217b is provided on the image-side surface.

For the anti-reflective coatings 217a and 217b, any of various types of known anti-reflective coatings may be used. For example, the anti-reflective coatings 217a and 217b may be formed by depositing a film of $SiO_2$, $Al_2O_3$, $TiO_2$, $ZrO_2$, or $MgF_2$ onto the protective glass 215, either individually or in multiple (approximately three to five) layers. Known anti-reflective coatings made up of these substances include, for example, a one-layer anti-reflective coating made of a thin film of $MgF_2$, a two-layer anti-reflective coating made of thin films of $ZrO_2$ and $MgF_2$ deposited in that order, and a three-layer anti-reflective coating made of thin films of $Al_2O_3$, $ZrO_2$, and $MgF_2$ deposited in that order. Also, in general, an anti-reflective coating is often formed by depositing approximately seven layers of the above substances or the like. For the anti-reflective coatings 217a and 217b, any known type of anti-reflective coating, including the above, may be used.

Note that, other than being provided with the anti-reflective coatings 217a and 217b on the object-side surface and the image-side surface of the protective glass 215, the image sensor 211 may be configured similarly to a typical image sensor. Consequently, detailed description will be reduced or omitted for parts of the configuration that are not directly related to the present disclosure, such as the configuration of the pixel circuit, for example.

At this point, to confirm the advantageous effects of the anti-reflective coatings 217a and 217b according to the first embodiment, the inventors performed a ray tracing simulation using a computational model imitating the optical system 20 illustrated in FIG. 3. Specifically, in the optical system 20 illustrated in FIG. 3, for the case of light from the endoscope 110 incident on an optical system not provided with the anti-reflective coatings 217a and 217b (hereinafter referred to as the experimental optical system), light intensity was calculated for light that is reflected by the image-side surface of the protective glass 215, reflected again by one of the upstream optical members (such as the eyepiece lens 201, for example), and finally incident on the light receiving face 213, and also for light that is reflected by the object-side surface of the protective glass 215, reflected again by one of the upstream optical members (such as the eyepiece lens 201, for example), and finally incident on the light receiving face 213. In other words, in the experimental optical system, the received light intensity on the light receiving face 213 of stray light produced by reflections off the image-side surface and the object-side surface of the protective glass 215 was calculated, respectively. Also, for confirmation, light intensity was also calculated for light reflected by the light receiving face 213, reflected by one of the upstream optical members (such as the eyepiece lens 201, for example), and finally incident on the light receiving face 213 again.

The results are summarized in Table 1 below. Note that Table 1 indicates relative values, in which 100% is taken to be the received light intensity on the light receiving face 213 of stray light produced by reflections off the image-side surface of the protective glass 215.

TABLE 1

| Reflection site | Light receiving face | Image-side surface of protective glass | Object-side surface of protective glass |
|---|---|---|---|
| Received light intensity at light receiving face | 14% | 100% | 35% |

Furthermore, the inventors performed a separate ray tracing simulation imitating imaging conditions in which flare and the like actually was observed previously in captured images, and imaging conditions in which flare and the like was not observed. Additionally, for each set of imaging conditions, relative values of the received light intensity on the light receiving face 213 were calculated, in which 100% is taken to be the received light intensity on the light receiving face 213 of stray light produced by reflections off the image-side surface of the protective glass 215, similarly to Table 1, and a threshold value for the received light intensity at which visually confirmable flare and the like is produced was computed. As a result, it was demonstrated that when the received light intensity is expressed as a relative value according to a standard similar to Table 1, visually confirmable flare and the like is not produced if the relative value of the received light intensity is less than approximately 30(%).

The results indicated in Table 1 above demonstrate that since the relative value of the received light intensity on the light receiving face 213 of stray light produced by reflections off the light receiving face 213 of the photodiode is below 30(%), such stray light makes little to no contribution to the occurrence of flare and the like. On the other hand, the results indicated in Table 1 above demonstrate that since the relative value of the received light intensity on the light receiving face 213 of stray light produced by reflections off the image-side surface of the protective glass 215 and the relative value of the received light intensity on the light receiving face 213 of stray light produced by reflections off the object-side surface of the protective glass 215 are both greater than 30(%), such stray light may contribute greatly to the occurrence of flare and the like.

In contrast, in the first embodiment, as discussed earlier, the anti-reflective coatings 217a and 217b are provided on the image-side surface and the object-side surface of the protective glass 215. By providing the anti-reflective coatings 217a and 217b, very little light is reflected off the image-side surface and the object-side surface of the protective glass 215, and thus the relative values of the received light intensity on the light receiving face 213 produced by reflections off the image-side surface and the object-side surface of the protective glass 215 both become values far below 30(%). In this way, by providing the anti-reflective coatings 217a and 217b on the image-side surface and the object-side surface of the protective glass 215, a moderation in the occurrence of flare and the like was confirmed. Consequently, according to the first embodiment, a higher-quality captured image may be obtained.

The above thus describes the optical system 20 according to the first embodiment with reference to FIG. 3. However, the optical system 20 according to the first embodiment is not limited to the configuration illustrated in FIG. 3. Advantageous effects similar to the first embodiment described above may be obtained by providing an anti-reflective coating to the protective glass of an image sensor in an optical system provided in a camera head of a typical endoscopic device. Consequently, the configuration of the optical system 20 other than the protective glass 215 and the anti-reflective coatings 217a and 217b may be modified appropriately within the conceivable range of an optical system provided in a camera head of a typical endoscopic device.

In addition, in the example configuration of the optical system 20 described above, the anti-reflective coatings 217a and 217b are provided on both faces of the protective glass 215, but the first embodiment is not limited to such an example. Even if an anti-reflective coating is provided on only one of either the image-side surface or the object-side surface of the protective glass 215, the occurrence of stray light due to reflections off the surface provided with the anti-reflective coating may be moderated, and thus the occurrence of flare and the like may be moderated. In this case, referencing the results indicated in Table 1 above, in the case of providing the anti-reflective coating on only one of either the image-side surface or the object-side surface of the protective glass 215, providing the anti-reflective coating on the image-side surface may result in a greater effect of reducing the occurrence of flare and the like.

Also, as described with reference to FIG. 1, in the related art there is known, as a method for reducing the occurrence of flare and the like, a method of disposing the cover glass 803 of the camera head tilted by a predetermined angle with respect to a direction orthogonal to the optical axis (in other words, a method of disposing the cover glass 803 tilted by a predetermined angle with respect to the protective glass 815 of the image sensor 811). This method additionally may be applied to the optical system 20 according to the first embodiment. In other words, in the configuration of the optical system 20 illustrated in FIG. 3, the cover glass 203 may also be disposed tilted by a predetermined angle with respect to a direction orthogonal to the optical axis (namely, the z-axis direction). Consequently, by disposing the cover glass 203 tilted in addition to providing the anti-reflective coatings 217a and 217b, an advantageous effect of reducing the occurrence of flare and the like is obtained, and thus an even higher-quality captured image may be obtained.

Note that if anti-reflective coatings are not provided on the surfaces of optical member other than the protective glass 215 (such as the lenses 207a, 207b, 207c, 207d, and 207e, for example), stray light produced by reflections off these optical members may become a factor in the occurrence of flare and the like. Consequently, in the first embodiment, anti-reflective coatings are preferably provided on the surfaces of optical members other than the protective glass 215.

However, stray light produced by reflections off optical members positioned closer to the light receiving face 213 are thought to contribute more greatly to the occurrence of flare and the like. This is because the optical system 20 is configured to condense observation light onto the light receiving face 213 (in other words, to form an image of the target of observation on the light receiving face 213), and thus as light moves closer to the light receiving face 213, the image produced by the observation light (that is, the image of the target of observation) becomes clearer, whereas conversely, the image produced by the observation light is less distinct at positions farther away from the light receiving face 213. Consequently, stray light produced by reflections off an optical member close to the light receiving face 213 is more intense, and thereby produces distinct flare, or in other words, ghosting. Accordingly, when attempting to reduce the occurrence of flare and the like by providing anti-reflective coatings on optical members as in the first embodiment, the greatest advantageous effect may be obtained by providing an anti-reflective coating on the protective glass 215 positioned closer to the light receiving face 213.

3. Second Embodiment

A second embodiment of the present disclosure will now be described. Note that the second embodiment corresponds to a modification of the configuration of the image sensor 211 in the first embodiment described above. The configuration of the endoscopic device and the configuration of parts of the optical system other than the image sensor are similar to the first embodiment, and thus in the following description of the second embodiment, detailed description of items overlapping with the first embodiment will be reduced or omitted, and items differing from the first embodiment will be described primarily.

Figure 4:
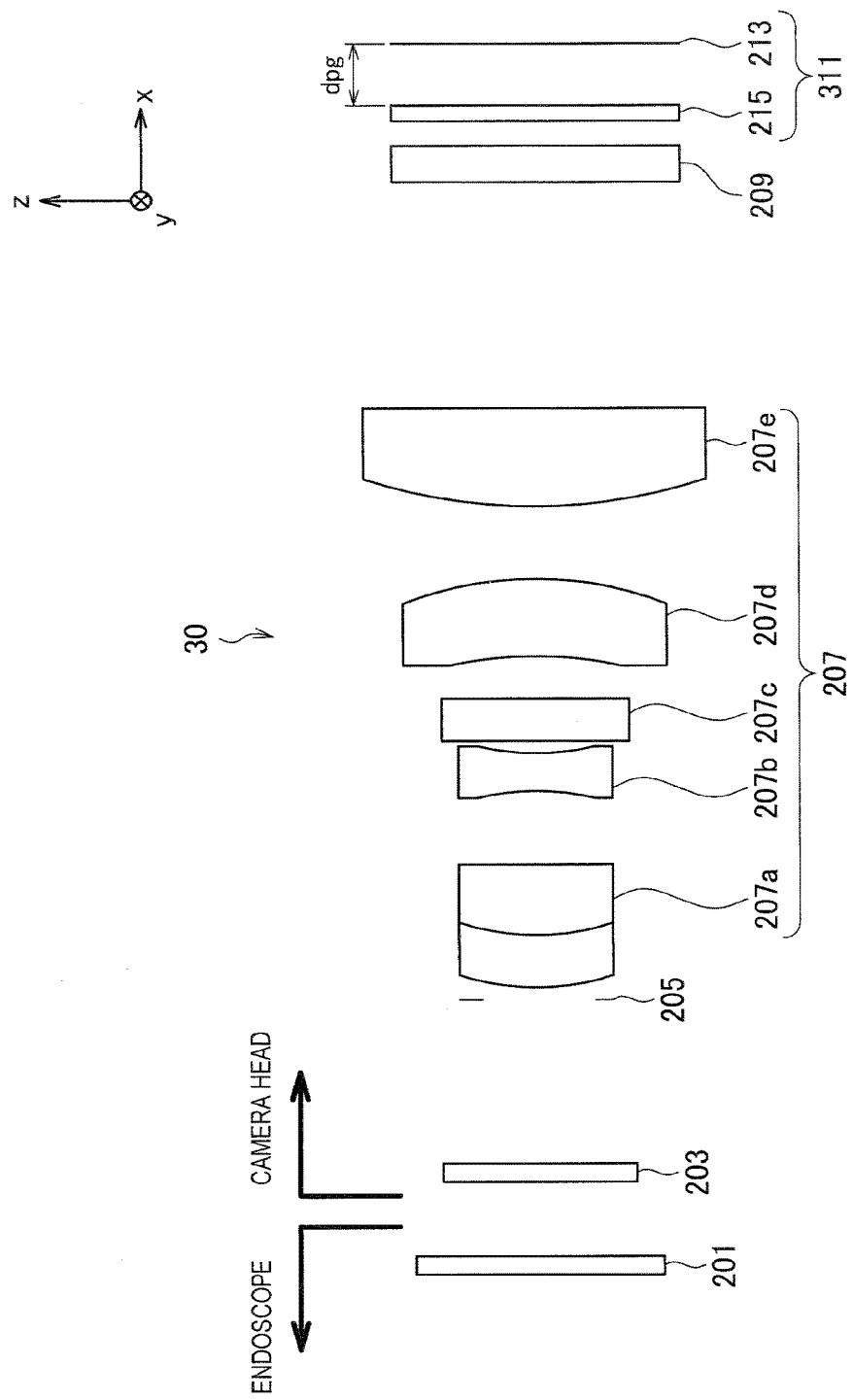
FIG. 4 is a diagram illustrating an example configuration of an optical system according to a second embodiment.

A configuration of the optical system according to the second embodiment will be described with reference to FIG. 4. FIG. 4 is a diagram illustrating an example configuration of the optical system according to the second embodiment. The optical system illustrated in FIG. 4 corresponds to an optical system made up of the various optical members existing from the eyepiece lens of the endoscope to the photodiode of the image sensor inside the camera head in an endoscopic device according to the second embodiment.

Referring to FIG. 4, the optical system 30 according to the second embodiment is equipped with an eyepiece lens 201, a cover glass 203, a diaphragm 205, a lens group 207, a filter 209, and a protective glass 215 of an image sensor 311. In FIG. 4, for the sake of clarity, the light receiving face 213 of the photodiode of the image sensor 311 is also illustrated. Note that the members other than the image sensor 311 illustrated in FIG. 4 have a configuration and function similar to the respective members in the optical system 20 according to the first embodiment illustrated in FIG. 3, and thus detailed description of these members will be reduced or omitted.

In the second embodiment, the configuration of the image sensor 311 is different from the first embodiment. Specifically, the image sensor 311 according to the second embodiment has a structure in which the protective glass 215 is disposed at least a predetermined distance away from the light receiving face 213. In the second embodiment, the distance dpg between the light receiving face 213 and the protective glass 215 is set to a larger value than that of the image sensor 211 according to the first embodiment or a typical CMOS sensor.

For example, in a typical CMOS image sensor, the distance dpg between the light receiving face 213 and the protective glass 215 is approximately from 0.3 to 0.5 (mm). In contrast, in the second embodiment, the image sensor 311 is configured so that this distance dpg is 1.0 (mm) or greater, for example (the reasoning for this numerical value will be discussed later).

Note that for the image sensor 311, other than the anti-reflective coatings 217a and 217b not being provided on the protective glass 215, and the distance between the light receiving face 213 and the protective glass 215 being enlarged, the configuration may be similar to the image sensor 211 according to the first embodiment. Consequently, detailed description will be reduced or omitted for parts of the configuration of the image sensor 311 that overlap with the image sensor 211.

At this point, as described in (2-2. Configuration of optical system) above, stray light produced by reflections off optical members positioned closer to the light receiving face 213 are thought to contribute more greatly to the occurrence of flare and the like. Consequently, by increasing the distance dpg between the light receiving face 213 and the protective glass 215, even if stray light is produced by reflections off the protective glass 215 and such stray light is incident on the light receiving face 213, the intensity of the incident light may be decreased, and the occurrence of flare and the like may be reduced.

To confirm the advantageous effects of disposing the protective glass 215 at least a predetermined distance from the light receiving face 213 according to the second embodiment, the inventors performed a ray tracing simulation using a computational model imitating the optical system 30 illustrated in FIG. 4. Specifically, in the experimental optical system used in the first embodiment, the received light intensity on the light receiving face 213 of stray light produced by reflections off the image-side surface of the protective glass 215 was calculated while varying the distance dpg between the light receiving face 213 and the protective glass 215.

The results are summarized in Table 2 below. Note that the experimental optical system used in the first embodiment corresponds to a distance dpg set to 0.5 (mm). In Table 2 below, the calculated received light intensity on the light receiving face 213 is indicated as relative values based on a standard similar to Table 1, or in other words, as relative values in which 100% is taken to be the received light intensity on the light receiving face 213 of stray light produced by reflections off the image-side surface of the protective glass 215 for the case in which the distance dpg is 0.5 (mm).

TABLE 2

| Distance dpg (mm) between light receiving face and protective glass | Received light intensity (%) on light receiving face (relative value) |
|---|---|
| 0.3 | 430 |
| 0.4 | 280 |
| 0.5 | 100 |
| 0.6 | 71 |
| 0.7 | 50 |
| 0.8 | 39 |
| 0.9 | 31 |
| 1.0 | 26 |
| 1.1 | 23 |
| 1.2 | 20 |
| 1.3 | 18 |
| 1.4 | 16 |
| 1.5 | 15 |

Figure 5:
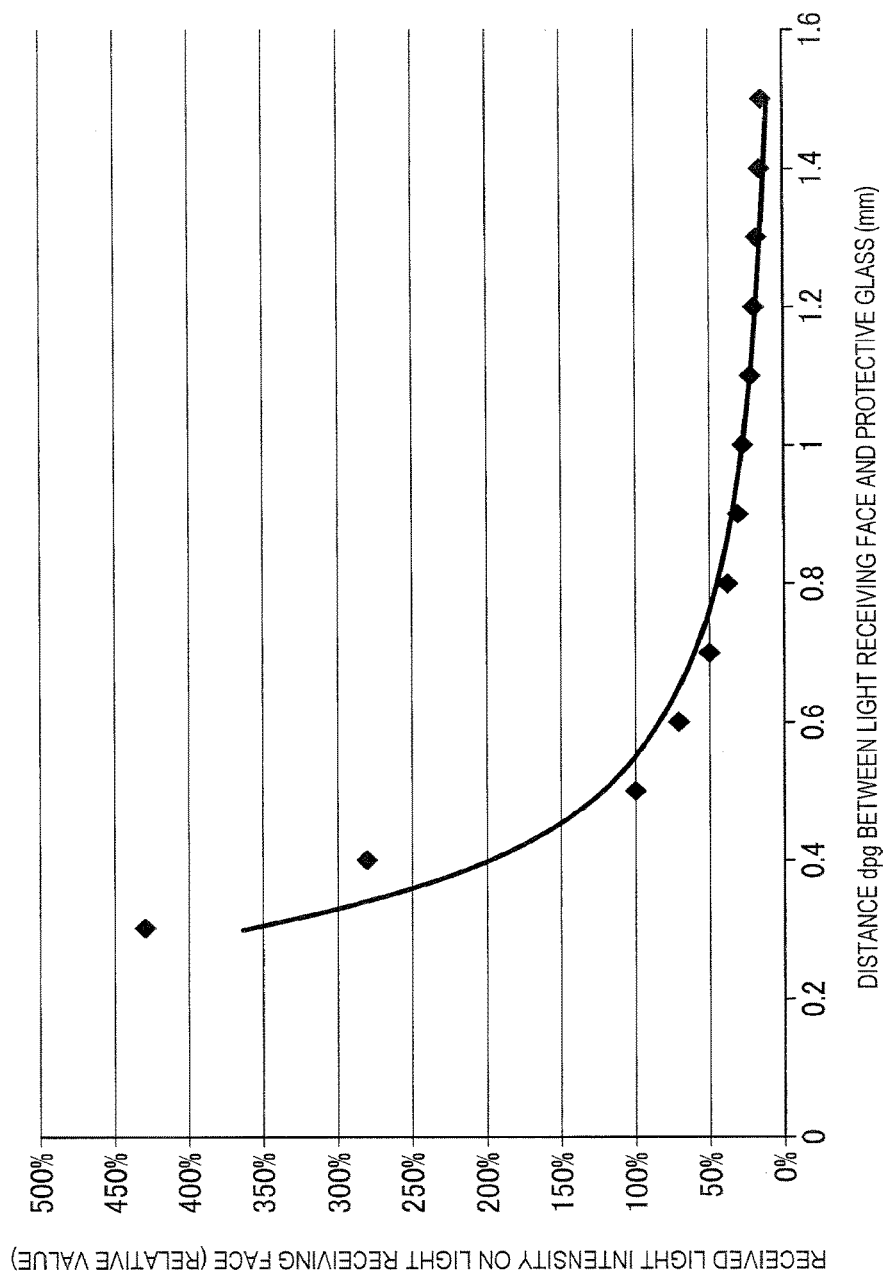
FIG. 5 is a graph illustrating a relationship between a distance dpg between a light receiving face and a protective glass, and a received light intensity on the light receiving face of stray light produced by reflections off the protective glass.

In addition, FIG. 5 illustrates a graph of the results indicated in Table 2. FIG. 5 is a graph illustrating the relationship between the distance dpg between the light receiving face 213 and the protective glass 215, and the received light intensity on the light receiving face 213 of stray light produced by reflections off the protective glass 215.

As Table 2 and FIG. 5 demonstrate, as the distance dpg between the light receiving face 213 and the protective glass 215 becomes larger, the received light intensity at the light receiving face 213 of stray light produced by reflections off the protective glass 215 becomes smaller. In the results indicated in Table 2 and FIG. 5, the relative value of the received light intensity on the light receiving face 213 of stray light becomes less than 30(%) when the distance dpg is at least 1.0 (mm). When evaluating the relative values of the received light intensity according to a similar standard as the first embodiment, the occurrence of flare and the like may be reduced to a non-visible level if the relative value of the received light intensity falls below 30(%). Consequently, according to the example configuration of the optical system 30 illustrated in FIG. 4, by making the distance dpg between the light receiving face 213 and the protective glass 215 at least 1.0 (mm), the occurrence of flare and the like may be reduced.

In this way, according to the second embodiment, by disposing the protective glass 215 at least a predetermined distance away from the light receiving face 213 in the image sensor 311, the occurrence of flare and the like may be reduced, making it possible to obtain a higher-quality captured image. This predetermined distance is determined according to the received light intensity on the light receiving face 213 of stray light produced by reflections off the protective glass 215, and in the example indicated in Table 2 above, is 1.0 (mm).

Note that the suitable value of the distance dpg between the light receiving face 213 and the protective glass 215 for appropriately reducing the occurrence of flare and the like may change, depending on factors such as the configuration of the optical system 30 and the anticipated intensity of observation light. The suitable value of the distance dpg may be designed appropriately by performing a ray tracing simulation using a computational model imitating an actual optical system, in accordance with actual usage conditions.

The above thus describes the optical system 30 according to the second embodiment with reference to FIG. 4. However, the optical system 30 according to the second embodiment is not limited to the configuration illustrated in FIG. 4. Advantageous effects similar to the second embodiment described above may be obtained by providing a configuration in which the protective glass of the image sensor is disposed at least a predetermined distance away from the light receiving face in an optical system provided in a camera head of a typical endoscopic device. Consequently, items other than the distance between the light receiving face 213 and the protective glass 215 in the optical system 30 may be modified appropriately within the conceivable range of an optical system provided in a camera head of a typical endoscopic device.

Additionally, likewise in the second embodiment, in the configuration of the optical system 30 illustrated in FIG. 4, the cover glass 203 may also be disposed tilted by a predetermined angle with respect to a direction orthogonal to the optical axis (namely, the z-axis direction). In other words, the cover glass 203 may also be disposed tilted by a predetermined angle with respect to the protective glass 215. Consequently, by disposing the cover glass 203 tilted in addition to the configuration in which the protective glass 215 is disposed at least a predetermined distance away from the light receiving face 213, an advantageous effect of reducing the occurrence of flare and the like is obtained, and thus an even higher-quality captured image may be obtained.

4. Third Embodiment

A third embodiment of the present disclosure will now be described. Note that the third embodiment corresponds to a modification of the configuration of the cover glass 203 and the configuration of the image sensor 211 in the first embodiment described above. The configuration of the endoscopic device and the configuration of parts of the optical system other than the cover glass and the image sensor are similar to the first embodiment, and thus in the following description of the third embodiment, detailed description of items overlapping with the first embodiment will be reduced or omitted, and items differing from the first embodiment will be described primarily.

Figure 6:
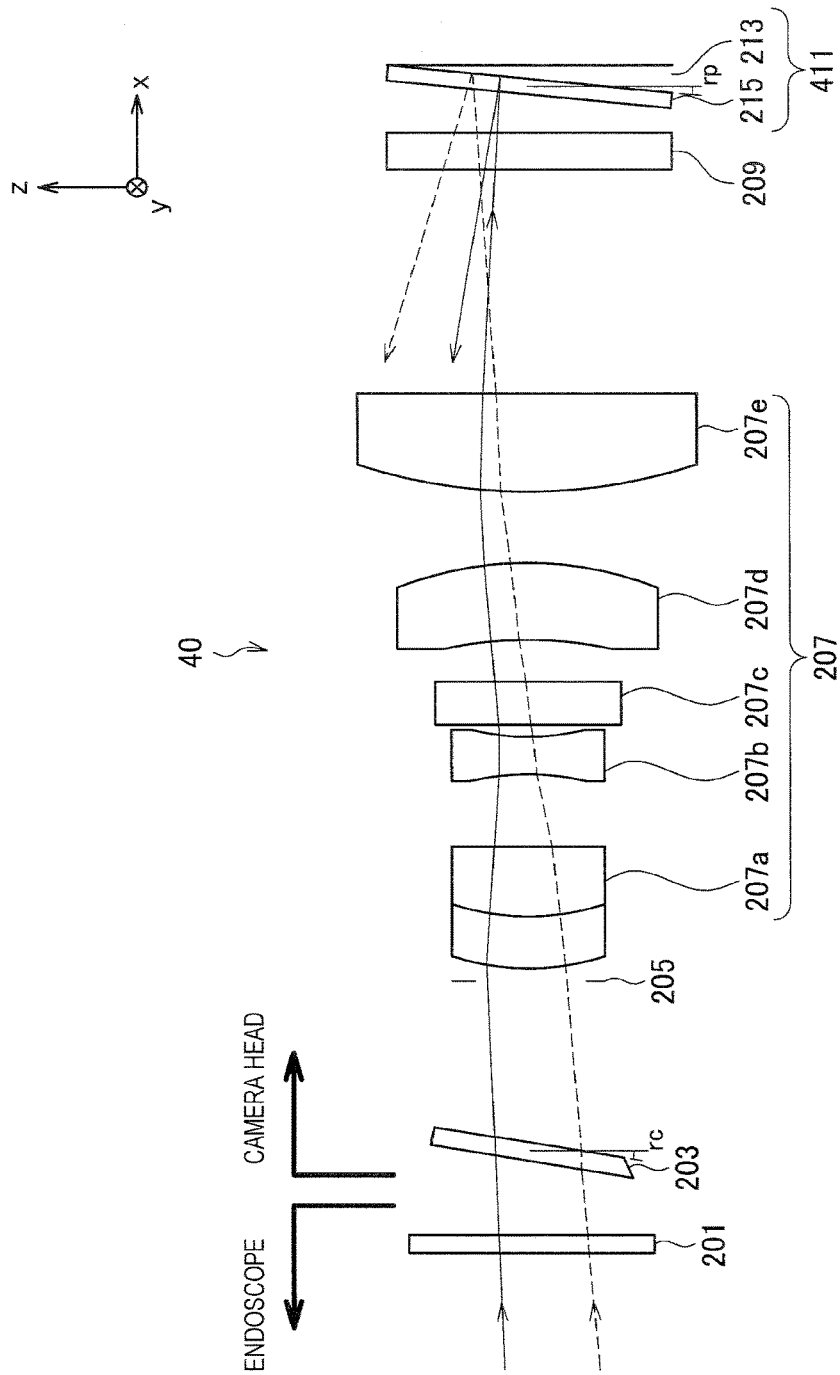
FIG. 6 is a diagram illustrating an example configuration of an optical system according to a third embodiment.

A configuration of the optical system according to the third embodiment will be described with reference to FIG. 6. FIG. 6 is a diagram illustrating an example configuration of an optical system according to the third embodiment. The optical system illustrated in FIG. 6 corresponds to an optical system made up of the various optical members existing from the eyepiece lens of the endoscope to the photodiode of the image sensor inside the camera head in an endoscopic device according to the third embodiment.

Referring to FIG. 6, the optical system 40 according to the third embodiment is equipped with an eyepiece lens 201, a cover glass 203, a diaphragm 205, a lens group 207, a filter 209, and a protective glass 215 of an image sensor 411. In FIG. 6, for the sake of clarity, the light receiving face 213 of the photodiode of the image sensor 411 is also illustrated. Note that the members other than the cover glass 203 and the image sensor 411 illustrated in FIG. 6 have a configuration and function similar to the respective members in the optical system 20 according to the first embodiment illustrated in FIG. 3, and thus detailed description of these members will be reduced or omitted.

In the third embodiment, the method of disposing the cover glass 203 and the configuration of the image sensor 411 are different from the first and second embodiments. Specifically, in the third embodiment, the cover glass 203 is disposed tilted by a predetermined angle rc with respect to a direction orthogonal to the optical axis (namely, the z-axis direction). Also, the image sensor 411 according to the third embodiment has a structure in which the protective glass 215 is disposed tilted by a predetermined angle rp with respect to the light receiving face 213. Note that such a structure in which the protective glass 215 is tilted by a predetermined angle rp with respect to the light receiving face 213 may be realized by appropriately modifying the structure of the package of the image sensor 411.

Note that for the image sensor 411, other than the antireflective coatings 217a and 217b not being provided on the protective glass 215, the cover glass 203 being disposed tilted by a predetermined angle rc with respect to a direction orthogonal to the optical axis, and the protective glass 215 being disposed tilted by a predetermined angle rp with respect to the light receiving face 213, the configuration may be similar to the image sensor 211 according to the first embodiment. Consequently, detailed description will be reduced or omitted for parts of the configuration of the image sensor 411 that overlap with the image sensor 211.

Similar to FIG. 1, FIG. 6 additionally illustrates a result of a ray tracing simulation executed using a computational model imitating the optical system 40. A comparison of the simulations illustrated in FIGS. 1 and 6 demonstrates that by disposing the protective glass 215 tilted by the predetermined angle rp, part of the observation light reflected by the protective glass 215 advances towards the outside of the lens group 207. The part of the reflected light that is not incident on the lens group 207 is not reflected again by an upstream optical member and incident on the image sensor 411. In this way, according to the third embodiment, since part of the stray light produced by reflections off the protective glass 215 is radiated towards the outside of the optical system 40, the received light intensity on the light receiving face 213 of such stray light may be decreased further, making it possible to further reduce the occurrence of flare and the like.

To confirm the advantageous effects of disposing the protective glass 215 tilted with respect to the light receiving face 213 according to the third embodiment, the inventors performed another ray tracing simulation using a computational model imitating the optical system 40 illustrated in FIG. 6. Specifically, in the computational model imitating the optical system 40 illustrated in FIG. 6, the received light intensity on the light receiving face 213 of stray light produced by reflections off the image-side surface of the protective glass 215 was calculated while varying the angle dp of the protective glass 215 with respect to the light receiving face 213.

Similar to the first and second embodiments, from the results of evaluating the received light intensity according to a standard in which 100% is taken to be the received light intensity on the light receiving face 213 of stray light produced by reflections off the image-side surface of the protective glass 215 indicated in Table 1, by making the angle dp approximately 6 (degrees) or greater, the relative value of the received light intensity may be made less than 30(%), or in other words, the occurrence of visually confirmable flare and the like may be reduced. In other words, according to the example configuration of the optical system 40 illustrated in FIG. 6, by making the angle rp of the protective glass 215 with respect to the light receiving face 213 approximately 6 (degrees) or greater, the occurrence of flare and the like may be reduced.

In this way, according to the third embodiment, by disposing the protective glass 215 tilted by at least a predetermined angle with respect to the light receiving face 213, the occurrence of flare and the like may be reduced, making it possible to obtain a higher-quality captured image. The predetermined angle is determined according to the received light intensity on the light receiving face 213 of stray light produced by reflections off the protective glass 215, and according the results of the current experiment, is 6 (degrees), for example.

Note that the suitable value of the angle rp of the protective glass 215 with respect to the light receiving face 213 for appropriately reducing the occurrence of flare and the like may change, depending on factors such as the configuration of the optical system 40 and the anticipated intensity of observation light. The suitable value of the angle rp may be designed appropriately by performing a ray tracing simulation using a computational model imitating an actual optical system, in accordance with actual usage conditions.

At this point, to obtain advantageous effects similar to the third embodiment, a configuration in which the entirety of the image sensor 411 is disposed tilted by a predetermined angle with respect to a direction orthogonal to the optical axis is also conceivable. Even with such a configuration, part of the observation light reflected by the protective glass 215 advances towards the outside of the lens group 207, and thus the received light intensity on the light receiving face 213 of stray light may be decreased. However, in the case of disposing the entirety of the image sensor 411 tilted, there is a risk of also lowering the received light intensity of the observation light that was originally supposed to be received on the light receiving face 213. Consequently, to ensure the received light intensity of the observation light that was originally supposed to be received while also lowering the received light intensity of stray light, among the configuration of the image sensor 411, it is preferable to dispose only the protective glass 215 tilted with respect to a direction orthogonal to the optical axis, as illustrated in FIG. 6.

In addition, in the example configuration illustrated in FIG. 6, the cover glass 203 is also disposed tilted by a predetermined angle rc with respect to a direction orthogonal to the optical axis. As described in (1. Investigation of existing configuration) above, with this configuration, the intensity of stray light reflected by the cover glass 203 and incident on the image sensor 211 again may be decreased, and thus an advantageous effect of further reducing the occurrence of flare and the like may be obtained. Note that at this point, the tilt angle rc of the cover glass 203 and the tilt angle rp of the protective glass 215 are preferably different from each other. If the tilt angle rc of the cover glass 203 and the tilt angle rp of the protective glass 215 are approximately equal, or in other words, if the cover glass 203 and the protective glass 215 are disposed approximately parallel, most of the light reflected by the protective glass 215, incident on the cover glass 203, and reflected by the cover glass 203 again returns to the protective glass 215, and thus there is a risk of insufficiently obtaining the advantageous effect of decreasing the received light intensity on the light receiving face 213 of stray light. For example, to further obtain the advantageous effect, the tilt angle rc of the cover glass 203 and the tilt angle of the protective glass 215 may be angles of different sign, or in other words, the tilt direction of the cover glass 203 and the tilt direction of the protective glass 215 may be opposite directions.

The above thus describes the optical system 40 according to the third embodiment with reference to FIG. 6. However, the optical system 40 according to the third embodiment is not limited to the configuration illustrated in FIG. 6. Advantageous effects similar to the third embodiment described above may be obtained by providing a configuration in which the protective glass of the image sensor is disposed tilted by at least a predetermined angle with respect to the light receiving face in an optical system provided in a camera head of a typical endoscopic device. Consequently, items other than the angle between the light receiving face 213 and the protective glass 215 in the optical system 40 may be modified appropriately within the conceivable range of an optical system provided in a camera head of a typical endoscopic device.

For example, as above, in the example configuration illustrated in FIG. 6, the cover glass 203 is also disposed tilted by a predetermined angle rc with respect to a direction orthogonal to the optical axis, but the third embodiment is not limited to such an example. For example, the cover glass 203 may also be disposed approximately orthogonal to the optical axis, similar to the first and second embodiments. Even with a configuration in which only the protective glass 215 of the image sensor 411 is tilted, the received light intensity on the light receiving face 213 of stray light produced by reflections off the protective glass 215 may be decreased, making it possible to reduce the occurrence of flare and the like.

At this point, in consideration of the basic principle of decreasing the received light intensity on the light receiving face 213 of stray light in the third embodiment, by disposing any optical member that may cause the production of stray light in the optical system 40, or in other words, any optical member not provided with an anti-reflective coating, tilted by at least a predetermined angle with respect to a direction orthogonal to the optical axis, part of the stray light is radiated towards the outside of the optical system 40, and thus similar advantageous effects may be obtained. The optical members that may cause the production of stray light in the optical system 40 are the eyepiece lens 201, the cover glass 203, and the protective glass 215. In other words, in the third embodiment, the members disposed tilted are not limited to the cover glass 203 and the protective glass 215, and the optical system 40 may also be configured so that at least one from among the eyepiece lens 201, the cover glass 203, and the protective glass 215 is disposed tilted by at least a predetermined angle with respect to a direction orthogonal to the optical axis.

However, in this case, it is not desirable for these members to be disposed so that the eyepiece lens 201, the cover glass 203, and the protective glass 215 are all approximately parallel to each other. This is because if any members among the eyepiece lens 201, the cover glass 203, and the protective glass 215 are disposed approximately parallel to each other, little to no component of stray light radiated outside the optical system 40 will exist in the reflections between those members, and thus the received light intensity on the light receiving face 213 of stray light may not be decreased effectively. Consequently, to more ideally obtain the advantageous effect of decreasing the received light intensity on the light receiving face 213 of stray light, the eyepiece lens 201, the cover glass 203, and the protective glass 215 preferably are disposed so as not to be approximately parallel to each other.

5. Conclusion

As described above, in the first to third embodiments, each of the image sensors 211, 311, and 411 is provided with a stray light intensity-reducing structure for decreasing the received light intensity on the light receiving face 213 of stray light produced by reflections of observation light off the protective glass 215 in the image sensor 211, 311, and 411, respectively. By providing a stray light intensity-reducing structure, the received light intensity on the light receiving face 213 of stray light is decreased, and the occurrence of flare and the like is reduced, thereby making it possible to obtain a higher-quality captured image.

Specifically, in the first embodiment, a structure in which an anti-reflective coating is provided on at least one face of the protective glass 215 of the image sensor 211 is provided as the stray light intensity-reducing structure. In the second embodiment, a structure in which the protective glass 215 of the image sensor 311 is disposed at least a predetermined distance away from the light receiving face 213 is provided as the stray light intensity-reducing structure. In the third embodiment, a structure in which the protective glass 215 of the image sensor 411 is disposed tilted by at least a predetermined angle with respect to the light receiving face 213 is provided as the stray light intensity-reducing structure.

Note that the respective configurations described in the first to third embodiments above may also be combined with each other where possible. By combining the respective configurations described in the first to third embodiment, an even greater advantageous effect of reducing flare and the like may be obtained, and a higher-quality captured image may be obtained.

By providing a stray light intensity-reducing structure and improving the quality of the captured image, the user of the endoscopic device 10 according to the first to third embodiments (a physician) becomes able to perform surgeries and examinations using the endoscopic device 10 more smoothly, and thus the user burden is lightened. Also, by improving the quality of the captured image, mistakes in procedures or diagnoses performed using the captured image may be reduced, and thus safer medical practice may be realized.

Herein, as described in (1. Investigation of existing configuration) above, in the endoscopic device 10, when the autoclave process is taken into account, it is impractical to provide an anti-reflective coating on the sites exposed to the outside, namely, the eyepiece lens 201 of the endoscope 110 and the cover glass 203 of the camera head 130. With a typical digital camera or the like, a method of providing an anti-reflective coating on all optical members constituting the optical system to reduce flare and the like has been proposed, but given the above reasons, adopting such a method in the endoscopic device 10 may not be possible.

Meanwhile, to ensure the ability to withstand autoclaving, the eyepiece lens 201 and the cover glass 203 are preferably formed from sapphire glass. Since sapphire glass has a greater reflectance compared to typical glass materials, in the endoscopic device 10, the occurrence of flare and the like may be exacerbated.

In this way, with the endoscopic device 10, flare and the like occurs more easily than in a typical digital camera or the like, but it is impractical to apply an effective method used in the past, namely, the method of providing an anti-reflective coating on all optical members. Consequently, with the endoscopic device 10, there is a strong demand for technology able to reduce the occurrence of flare and the like by a method other than providing an anti-reflective coating on the eyepiece lens 201 and the cover glass 203.

In contrast, as discussed above, in the first to third embodiments, by providing a stray light intensity-reducing structure in the image sensors 211, 311, and 411 inside the camera head 130, the occurrence of flare and the like is reduced. Consequently, even if providing an anti-reflective coating on the eyepiece lens 201 and the cover glass 203 is impractical as above, the occurrence of flare and the like may be reduced favorably, making it possible to obtain a higher-quality captured image.

6. Supplemental Remarks

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to an embodiment of the present disclosure can exhibit other effects that are evident to those skilled in the art along with or instead of the effects based on the present specification.

Additionally, the present technology may also be configured as below.

(1) A endoscopic camera head including:
a cover glass, provided on a connecting face that connects to a base of an endoscope, and disposed to cover an opening for taking into a housing observation light guided inside a lens barrel of the endoscope to the base; and
an image sensor configured to receive the observation light passing through the cover glass and entering the housing, and capture an image of a target of observation, wherein
in the image sensor, an anti-reflective coating is provided on at least one face of a protective glass disposed facing opposite a light receiving face configured to receive the observation light.

(2) The endoscopic camera head according to (1), wherein
in the image sensor, the protective glass is disposed at least a predetermined distance away from the light receiving face, and
the predetermined distance is determined according to an intensity of stray light produced by a reflection of the observation light off the protective glass.

(3) The endoscopic camera head according to (1) or (2), wherein
in the image sensor, the protective glass is disposed tilted by at least a predetermined angle with respect to the light receiving face.

(4) The endoscopic camera head according to any one of (1) to (3), wherein
the cover glass is disposed tilted by a predetermined angle with respect to the protective glass of the image sensor.

(5) The endoscopic camera head according to any one of (1) to (4), wherein
the cover glass is made of sapphire glass.

(6) The endoscopic camera head according to any one of (1) to (6), wherein
at the base of the endoscope, an eyepiece lens is provided at a position facing opposite the cover glass.

(7) The endoscopic camera head according to (6), wherein
the eyepiece lens, the cover glass, and the protective glass are disposed so as not to be approximately parallel to each other.

(8) The endoscopic camera head according to (6) or (7), wherein
the eyepiece lens is made of sapphire glass.

(9) An endoscopic camera head including:
a cover glass, provided on a connecting face that connects to a base of an endoscope, and disposed to cover an opening for taking into a housing observation light guided inside a lens barrel of the endoscope to the base; and
an image sensor configured to receive the observation light passing through the cover glass and entering the housing, and capture an image of a target of observation, wherein
in the image sensor, the protective glass is disposed at least a predetermined distance away from the light receiving face, and the predetermined distance is determined according to an intensity of stray light produced by reflections of the observation light off the protective glass.

(10) An endoscopic camera had including:
a cover glass, provided on a connecting face that connects to a base of an endoscope, and disposed to cover an opening for taking into a housing observation light guided inside a lens barrel of the endoscope to the base; and
an image sensor configured to receive the observation light passing through the cover glass and entering the housing, and capture an image of a target of observation, wherein
in the image sensor, the protective glass is disposed tilted by at least a predetermined angle with respect to the light receiving face.

What is claimed is:
1. An endoscopic camera head removably connectable to an endoscope comprising:
a cover glass disposed to cover an opening for taking into a housing observation light from the connected endoscope; and
an image sensor configured to receive the observation light passing through the cover glass and entering the housing, and capture an image of a target of observation, wherein
the image sensor including a light receiving face that is configured to receive the observation light and a protective glass that is disposed opposite the light receiving face,
in the image sensor, an anti-reflective and light pass-through coating is provided on at least one face of the protective glass, and the anti-reflective and light pass-through coating is configured to moderate reflections of the observation light from the at least one face of the protective glass.

2. The endoscopic camera head according to claim 1, wherein in the image sensor, the protective glass is disposed at least a predetermined distance away from the light receiving face, and the predetermined distance is determined according to an intensity of stray light produced by a reflection of the observation light off the protective glass.

3. The endoscopic camera head according to claim 1, wherein in the image sensor, the protective glass is disposed tilted by at least a predetermined angle with respect to the light receiving face.

4. The endoscopic camera head according to claim 1, wherein the cover glass is disposed tilted by a predetermined angle with respect to the protective glass of the image sensor.

5. The endoscopic camera head according to claim 1, wherein the cover glass is made of sapphire glass.

6. An endoscopic device, comprising:

an endoscopic camera head including:

a cover glass disposed to cover an opening for taking into a housing observation light, and an image sensor configured to receive the observation light passing through the cover glass and entering the housing, and capture an image of a target of observation, wherein the image seonsor including a light receiving face that is configured to receive the observation light and a protective glass that is disposed opposite the light receiving face, in the image sensor, an anti-reflective and light pass-through coating is provided on a at least one face of the protective glass and the anti-reflective and light pass-through coating is configured to moderate reflections of the observation light from the at least one face of the protective glass; and an endoscope removably connectable to the endoscopic camera head and which guides the observation light into the housing of the endoscopic camera head, the endoscope including an eyepiece lens that is provided at a position facing opposite the cover glass.

7. The endoscopic device according to claim 6, wherein the eyepiece lens, the cover glass, and the protective glass are disposed so as not to be approximately parallel to each other.

8. The endoscopic device according to claim 6, wherein the eyepiece lens is made of sapphire glass.

* * * * *